United States Patent
Wand et al.

Patent Number: 5,178,791
Date of Patent: Jan. 12, 1993

[54] HALOGENATED DIPHENYLDIACETYLENE LIQUID CRYSTALS

[75] Inventors: Michael D. Wand, Boulder, Colo.; Sean D. Monahan, Madison, Wis.

[73] Assignee: Displaytech, Inc., Boulder, Colo.

[21] Appl. No.: 667,668

[22] Filed: Mar. 11, 1991

[51] Int. Cl.$^5$ .................. C09K 19/06; C09K 19/52
[52] U.S. Cl. .................. 252/299.6; 252/299.01; 568/647
[58] Field of Search .................. 252/299.01, 299.6; 568/647

[56] References Cited

U.S. PATENT DOCUMENTS

| | | | |
|---|---|---|---|
| 4,431,263 | 2/1984 | Garito | 385/143 |
| 4,778,458 | 3/1988 | Higuchi et al. | 252/299.65 |
| 4,895,975 | 1/1990 | Fujiwara | 560/83 |

FOREIGN PATENT DOCUMENTS

| | | |
|---|---|---|
| 0220747 | 5/1987 | European Pat. Off. |
| 0269062 | 6/1988 | European Pat. Off. |
| 0278665 | 8/1988 | European Pat. Off. |
| 3901266 | 7/1990 | Fed. Rep. of Germany |
| 63-054336 | 3/1988 | Japan |
| 62-384147 | 11/1988 | Japan |
| 8606373 | 11/1986 | PCT Int'l Appl. |
| 8705018 | 8/1987 | PCT Int'l Appl. |
| 8902425 | 3/1989 | PCT Int'l Appl. |

OTHER PUBLICATIONS

Grant et al., (1978), Mol. Cryst. Liq. Cryst., 48:175–182.
Barrall et al., (1978), Liq. Cryst. Ordered Fluids, 3:19–39.

Primary Examiner—Robert L. Stoll
Assistant Examiner—C. Harris
Attorney, Agent, or Firm—Greenlee & Winner

[57] ABSTRACT

The present invention provides liquid crystals that are 3,3'-dihalogenated diphenyldiacetylenes of the general formula:

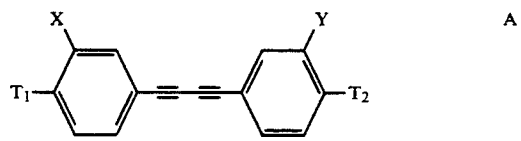

where X and Y are, independently of one another, a halogen atom and $T_1$ and $T_2$, independently of one another are alkyl or alkenyl or alkoxy tail groups, $R_1$, $R_2$, or $OR_3$, respectively, wherein $R_1$ and $R_3$, independently of one another, are straight-chain or branched alkyl groups having three to twenty carbon atoms and $R_2$ is a mono or diene which may be branched or straight-chain having three to twenty carbon atoms. $R_1$, $R_2$, or $R_3$ may be substituted with one or more halogens, particularly fluorines, except that the C-1 carbon of an $OR_3$ tail may not be halogenated. One or two non-neighboring $CH_2$ groups of $R_1$ or $R_3$ may be substituted with an O atom, except that the C-1 $CH_2$ group of an $OR_3$ tail may not be substituted with an O atom. Liquid crystals in which $X=Y=$fluorine and $T_1=T_2$ are more preferred. Compounds in which $R_1$, $R_2$ and $R_3$ are straight-chain alkyl groups or ω-monoene groups are more preferred.

29 Claims, No Drawings

HALOGENATED DIPHENYLDIACETYLENE LIQUID CRYSTALS

This invention was made with partial support of the United States Government. The United States Government has certain rights in this invention.

FIELD OF THE INVENTION

The present invention is in the field of liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. Liquid crystal displays have a number of unique characteristics, including low voltage and low power of operation, which make them perhaps the most promising candidate materials for non-emissive electro-optical displays available with current technology. Most of these devices are based upon the dielectric alignment effects in nematic, cholesteric and smectic phases of the liquid crystal compound in which, by virtue of dielectric anisotropy, the average molecular long axis of the liquid crystal molecules take up a preferred orientation in an applied electric field. Since the coupling to the applied filed by this mechanism is rather weak, the resultant electro-optical response may be too slow for many potential applications. The requirement for speed may become especially important in proportion to the number of elements which have to be addresses in a device. This may result in increasingly impractical production costs for the potential use of such devices in flat-panel displays for use in video terminals, oscilloscopes, radar and television screens.

Electro-optic effects with sub-microsecond switching speeds can be achieved using the technology of ferroelectric liquid crystals (FLCs) of N.A. Clark and S.T. LagerWall (1980) Appl. Phys. Lett. 36:899 and U.S. Pat. No. 4,367,924. These investigators have reported display structures prepared using FLC materials having not only high speed response (about 1,000 times faster than currently used twisted nematic devices), but which also exhibit bistable, threshold sensitive switching. Such properties make FLC-based devices excellent candidates for light modulation devices including matrix addresses light valves containing a large number of elements for passive displays of graphic and pictorial information, optical processing applications, as well as for high information content dichroic displays. A review of the applications of FLC devices is given by S.T. Lagerwall and N.A. Clark (1989) Ferroelectrics 94:3-62.

Tilted smectic liquid crystal phases, in particular smectic C phases, are useful in the preparation of FLC materials. Materials exhibiting such smectic phases which comprise chiral, nonracemic components possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In FLC devices, such as the Surface Stabilized FLC cells (SSFLC) of Clark and Lagerwall, appropriate application of an external electric field results in alignment of the molecules in the FLC phase with the applied filed. When the sign of the applied field is reversed, realignment or switching of the FLC molecules occurs. This switching can be employed for light modulation. Within a wide range of electric field strengths, the switching speed (optical rise time) is inversely proportional to applied field strength and polarization or dipole density (P), and directly proportional to orientational viscosity. Faster switching speeds are thus associated with FLC phases which possess higher polarization density and lower orientational viscosity.

A basic requirement for application of ferroelectric liquid crystals in such devices is the availability of chemically stable LC compounds or mixtures which exhibit chiral tilted smectic phases, preferably chiral smectic C phases, over a substantial temperature range, preferably about room temperature. In some cases, a chiral nonracemic LC material will possess an enantiotropic or monotropic chiral tilted smectic phase. FLC mixtures possessing chiral smectic phases, including those with smectic C* phases (i.e, chiral smectic C), with useful temperature ranges can also be obtained by admixture of chiral, nonracemic compounds, designated FLC dopants, into liquid crystal host material which exhibits a desired tilted smectic phase (an FLC host material) and which may or may not be composed of chiral molecules. Addition of the FLC dopant can affect the ferroelectric polarization density and/or the viscosity of the resultant FLC mixture and thereby affect switching speed. Desirable FLC dopants are molecules which impart high ferroelectric polarization density to an FLC mixture without significantly increasing the orientational viscosity of the mixture. Components of FLC mixtures can also be adjusted to vary phase transition temperatures or ranges.

Other properties of the FLC material, for example the tilt angle of the chiral smectic phase and the birefringence of the material, can affect their usefulness for particular device applications. These properties are affected by the structures of the various components and the amounts of these components in the FLC material. Most effort in the development of FLC materials has been directed toward flat panel display applications. The optimal characteristics for FLC materials used in such displays include high spontaneous polarization (Ps) and low orientational viscosity to achieve fast switching, tilt angles of 22.5° which result in maximum contrast in SSFLC cells switched between crossed polarizers, low birefringence which facilitates construction of a desirable thickness panel and broad temperature range (about room temperature). FLC materials useful in waveguides, integrated optics and spatial light modulators have somewhat different requirements. High polarization and low viscosity are desired for both display and optical switching FLC applications. Enhanced performance in optical switching FLC applications is correlated with high total refractive index change between the switched states which is associated with high birefringence and large tilt angles. A particular type of FLC display device, a dichroic display device containing color switching elements incorporating mixtures of FLCs with dichroic dyes, also requires high tilt FLC material to achieve highest contrast. (See Ozaki et al. (1985) Jpn. J. Appl. Phys. Part I 24 (Suppl. 24-3):63-65.) For applications requiring high tilt angle and/or high birefringence it is desirable to have FLC materials which combine these properties with fast switching speed and broad room temperature smectic C* phases.

Thermotropic liquid crystal molecules typically possess structures which combine a rigid core coupled with two relatively "floppy", i.e., structurally flexible, tails. The tails are typically coupled to the core such that the LC molecule can assume a configuration with relatively linear arrangement of the tails along the long axis of the core. (See Demus et al. (1974) Flussige Kristalle In Tabellen, VEB Deutscher Verlag fur Grundstoffindustrie, Lebzig.) FLC materials have been prepared by introduction of a stereocenter into one of the tails, thus introducing chirality. A variety of FLC materials including materials having phenylbenzoate, biphenyl, phenylpyrimidine, and phenylpyridine core structures have been reported. FLC host materials, having low polarization density or which are achiral, having such core structures have also been reported. FLC host materials typically possess smectic C phases. A number of chiral nonracemic FLC dopant materials are known in the art.

FLC compositions having tilt angles between 30° to 60° have been reported by Ichihashi et al. (1988) EPO publication No. 269,062. The authors infer that tilt angle in the smectic C phase depends on the ordering of liquid crystal phases exhibited by a material, in particular the absence of a higher temperature smectic A phase, is associated with high tilt in the smectic C phase. The reference provides the tilt angles of a number of smectic C phase LCs, no correlation between tilt angle and structure is disclosed. A related EPO application of Furukawa et al. (1988) Publication No. 220,747, refers to a method for controlling tilt angle in FLC smectic C mixtures. The method described involves controlling the tilt angle of a mixture by adjusting the composition of the mixture such that a smectic A phase is present (for low tilt mixtures) or absent (for high tilt mixtures). These reference also refer to a number of components of LC mixtures some of which components have monofluorinated core moieties.

Diacetylenic liquid crystals have been reported by B. Grant (1978) Mol. Cryst. Liq. Cryst. 48:175–182 and E.M. Barrall et al. (1978) Liq. Cryst. Ordered Fluids 3:19–39. Symmetric 4,4'-substituted diphenyldiacetylenes having the general formula:

R—Ph—C≡C—C≡C—Ph—R where R=n-alkyl or n-alkoxy were reported to have liquid crystal properties. The alkyl substituted derivatives were reported to exhibit only nematic liquid crystal phases. No smectic phases were reported with the alkyl derivatives. Most of the alkoxy derivatives similarly exhibited only nematic LC phases, however, the and n-$C_{14}H_{29}O$ and n-$C_{15}H_{31}O$ derivatives were reported to display two smectic phases, over a narrow temperature range with the following phase diagrams, respectively:

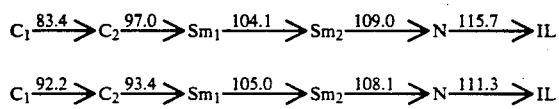

where C=crystal, N=nematic, Sm=smectic and IL-=isotropic liquid and temperatures are in °C. Barrall et al. supra reports that $Sm_1$ appears to be a "tilted smectic B phase" and speculates that $Sm_2$ is a smectic C phase.

Grant supra (1978) also reports the para-substituted phenylacetylenes:

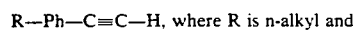

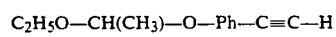

which are employed in the synthesis of the alkyl and alkoxy-substituted diphenyldiacetylenes described.

Gray et al. (1989) WO 89/02425 refers to laterally fluorinated oligophenyls useful as liquid crystals which are biphenyls or terphenyls. Formula III, refers to tolanes, i.e.,:

where laterally fluorinated 1,4-benzene rings are included in the listing of L and E. Formula 3.1 refers to a monofluorinated tolane of formula:

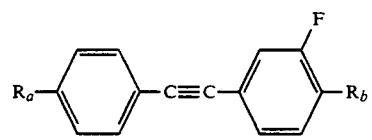

where $R_a$ and $R_b$ may be alkyl or alkoxy.

Higuchi et al. U.S. Pat. No. 4,728,458 refers to chiral polyphenyl compounds useful in liquid crystal materials. The general formula (1) refers to halogenation of the core moiety which core appears to include tolanes: —Ph—C≡C—Ph—. However, no tolanes appear to be specifically disclosed therein.

Eidenschink et al. WO 87/05018 refers to optically active compounds and the general formula I appears to refer to cores containing halogenated 1,4 phenylene groups and appears to refer to tolane cores. A related application of Krause et al. WO 86/06373 refers in formula I to halogenation of cores containing nitrogen containing heterocycles.

Saito et al. (1988) EP published application 278,665 refers to chiral 2-substituted alkyl ethers useful as components in LC compositions which include those having 3,3'-halogenated biphenyl cores.

SUMMARY OF THE INVENTION

The present invention provides liquid crystals that are 3,3'-dihalogenated diphenyldiacetylenes of the general formula:

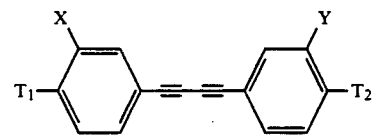

where X and Y are, independently of one another, a halogen atom and $T_1$ and $T_2$, independently of one another are alkyl or alkenyl or alkoxy tail groups, $R_1$, $R_2$, or $OR_3$, respectively, wherein $R_1$ and $R_3$, independently of one another, are straight-chain or branched alkyl groups having three to twenty carbon atoms and $R_2$ is a mono or diene which may be branched or straight-chain having three to twenty carbon atoms. $R_1$, $R_2$, or $R_3$ may be substituted with one or more halogens, particularly fluorines, except that the C-1 carbon of an $OR_3$ tail may not be halogenated. One or two non-neighboring CH₂ groups of $R_1$ or $R_3$ may be substituted with an O atom, except that the C-1 CH₂ group of an OR₃ tail may not be substituted with an O atom. Liquid crystals in which X=Y=fluorine and $T_1=T_2$ are more preferred. Compounds in which $R_1$, $R_2$ and $R_3$ are straight-chain alkyl groups or ω-monoene groups are more preferred.

In particular, the present invention provides 4, 4'-disubstituted 3,3'-difluorodiphenyldiacetylenes of formula:

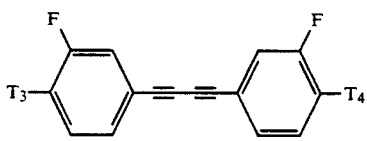

B where $T_3$ and $T_4$, independently of one another, are straight-chain or branched alkyl or alkoxy groups, $R_4$ or $OR_5$, having from three to twenty carbons atoms, wherein one of the C—C single bonds of $R_4$ may be substituted with a double bond with substitution at the ω-position being preferred. $R_4$ and $R_5$ groups which are stright-chain alkyl groups are more preferred.

More specifically, the present invention provides 4, 4'-disubstituted-3,3'-difluoro diphenyldiacetylenes of the formula:

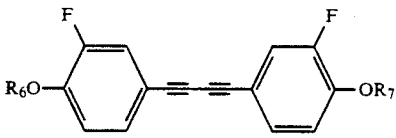

C wherein $R_6$ and $R_7$ are, independently of one another, straight-chain or branched alkyl groups having from three to twenty carbon atoms. Compounds in which $R_6$ and $R_7$ are straight-chain alkyl groups having three to twenty carbon atoms are preferred. Compounds in which $R_6$ and $R_7$ are straight-chain alkyl groups having nine to sixteen carbon atoms are more preferred. Most preferably $R_6=R_7$.

At least one of the tail groups of the compounds of formulas A, B or C may be a chiral, non-racemic group.

The compounds of the present invention are generally useful as liquid crystal materials or as components of liquid crystal materials. Compounds of formula C and mixtures thereof are useful as FLC host materials, in particular those compounds which exhibit a broad smectic C phase at temperatures close to room temperature are most useful.

Compounds of the present invention are useful alone or in combination with one another or with other liquid crystal components to provide FLC host materials and FLC materials. Compounds of formula C can, for example, be admixed to prepare mixtures having more desirable mesomorphic properties, i.e, broader smectic C phases and/or smectic C phases close to room temperature. FLC host materials comprising one or more of the compounds of formula C can be admixed with any of a variety of FLC dopants to prepare FLC materials having fast switching speeds. In particular, materials comprising about 50% or more by weight of a mixture of one or more of the components of formula C and substantially retaining a smectic C phase preferably extending over a range of 5° C. or more will be useful as FLC hosts.

Additionally, the 3,3'-difluorodiphenyldiacetylenes of the present invention are useful in the preparation of FLC materials having high optical tilt angles (i.e., about 30° or greater with an angle approaching 45° most preferred).

3,3'-Dihalodiphenyldiacetylenes of the present invention are also useful as components of FLC materials which increase the birefringence of the resulting mixture. In particular, the 3,3'-difluorodiphenyldiacetylenes of the present invention are useful for increasing birefringence in mixtures which retain desirable mesophoric properties, i.e., smectic C phases.

High birefringence FLC's of the present invention preferrably contain 30% or more by weight of a mixture of one or more of the 3,3'-difluorodiphenyldiacetylenes of formula C.

The present invention also provides 4-alkoxy, 3-fluorophenylacetylenes of formula:

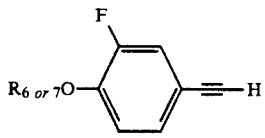

D wherein $R_6$ and $R_7$ are as defined above for formula C. These compounds are useful as intermediates in the synthesis of symmetric diphenyldiacetylenes of formula C.

DETAILED DESCRIPTION OF THE INVENTION

The 4,4'-disubstituted 3,3'-dihalogenated diphenyldiacetylenes of the present invention are prepared as exemplified in Scheme I for dialkoxy-3, 3'-difluorinated diphenyldiacetylenes.

Generally, as shown in Scheme I, an appropriately substituted phenylbromide (such as II) is coupled to a TMS-protected acetylene followed by deprotection to give a desired 4-substituted 3-halophenylacetylene (such as IV). Two molecules of the phenylacetylene are then coupled to produce a diphenyldiacetylene (such as V).

The compounds of formulas A, B and C can be readily synthesized by choice of starting material and/or by adaptation of the methods of Scheme I. For example, the 3,3'-dichlorodiphenylacetylenes can be readily prepared from the 3-chlorine analogs of the 4-alkoxyphenylbromides of formula II. A variety of alkyl, alkenyl and alkylether groups can be readily substituted for RO in Scheme I. For example, an ω-alkeneoxy group can be introduced in a compound of formula II by use of the ω-alkeneol as ROH. The phenylacetylene compounds of formula D, including those of formula IV, are intermediates in the preparation of fluorinated diphenyldiacetylenes. These intermediates need not be isolated in pure form in order to be useful in the synthesis of the difluorodiphenyldiacetylenes of the present invention.

Those of ordinary skill in the art will appreciate that other methods can be applied or readily adapted to the synthesis of compounds of formulas A, B and C. For example, the methods of Grant (1978) supra and methods referred to therein may be employed or readily adapted, in particular to the synthesis of symmetric diphenyldiacetylenes. Several methods of synthesis of unsymmetric diphenylacetylenes, which include for example,

SCHEME I

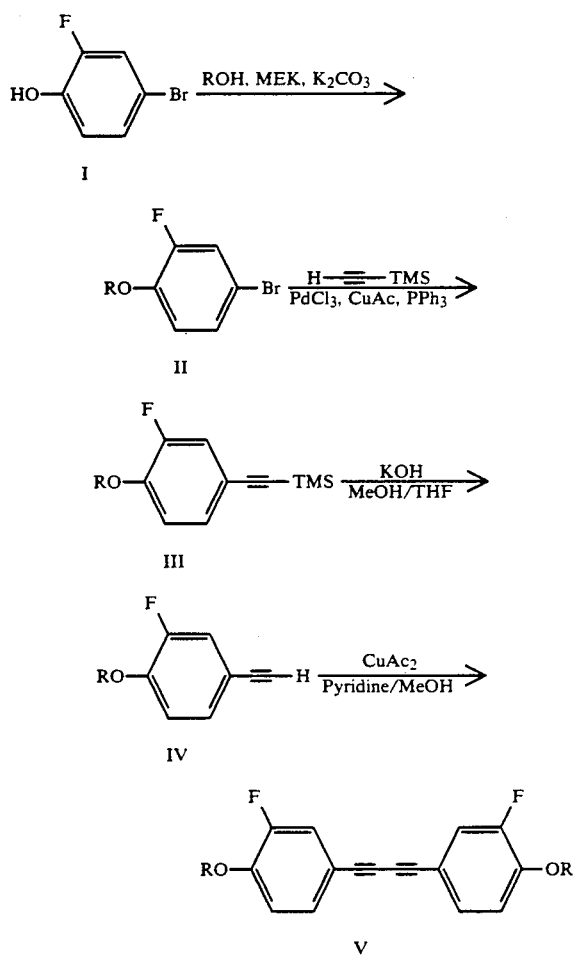

compounds C where $T_1 \neq T_2$ have been reported. (See: H. Shindo et al. (1990) J. Chem. Soc. Chem. Comm. 760 and J. Tsibouklis et al. (1988) Chemtronics 3:211.) Such methods can be readily adapted by choice of reagents or starting materials to the preparation of compounds of the present invention.

FLC materials are chiral nonracemic materials which exhibit a chiral tilted smectic phase, preferably a smectic C* phase. Such materials may be composed of a single chiral nonracemic FLC or may be a mixture of components. For example, a chiral nonracemic FLC dopant can be mixed with an FLC host which exhibits a smectic C phase to produce a chiral nonracemic FLC material. Such FLC materials are useful in optical devices such as those described by Clark and Lagerwall (supra), Surface Stabilized Ferroelectric Liquid Crystal Cells (SSFLC). FLC materials preferably display a fast switching speed in such devices. It is preferred that the FLC materials display a smectic C* phase. It is also preferred that the FLC materials do not exhibit higher order smectic phases. For use in such devices, it is preferred that the smectic C* phase extend at least over about 5° C. It is more preferred that the smectic C* phase extend over about 20° or more. A material having a smectic C* phase close to room temperature is desirable for use in devices which are intended for use at or near room temperature (20°-25° C). It is most desirable in such applications to have a material which displays a smectic C* phase; the temperature range of which spans room temperature.

FLC hosts are single compounds or multi-component mixtures which may or may not be chiral and nonracemic. Generally, FLC host materials exhibit a smectic C phase. If chiral and nonracemic, an FLC host generally has low polarization density. Chiral nonracemic FLC dopants, compatible for mixing with the host, are added to enhance the polarization density and decrease switching speed of the mixture. A variety of chiral nonracemic FLC dopants have been described. Dopants are admixed with the FLC host at a level which maximizes the polarization density of the resultant mixture, without significant adverse effect on the desired phase (or other) properties of the resultant mixture. For example, significant narrowing of the smectic C phase is generally to be avoided. Significant shifting of the smectic C phase away from room temperature for applications at or near room temperature is undesirable. The phase properties of the resultant FLC mixtures are most preferably thermodynamically stable. The amount of a dopant which can be added to a particular host material also depends on the solubility or mescribility of the dopant in the host.

The mesophoric and other properties (including tilt angle, birefringence and switching speed) of an FLC material can be adjusted for use in a particular application by addition of components to a mixture or by adjusting the concentration of components in the mixture. Examples of FLC dopants include, among others, those with phenylpyridine, phenylpyrimidine, and phenylbenzoate cores as described, for example, in: Walba and Vohra U.S. Pat. Nos. 4,705,874 and 4,638,073; Walba and Razavi U.S. Pat. No. 4,695,650; Walba and Eidman U.S. Pat. No. 4,777,280; Sakaguchi et al U.S. Pat. Nos. 4,909,957 and 4,973,425; Hemmerling et al. U.S. Pat. No. 4,876,028

The dihalodiphenylacetylene compounds of the present invention are additionally found to impart increased birefringence to FLC mixtures. Birefringence (or Δn) of a mixture in the smectic C phase is measured by conventional methods, such as those employing an Abbe Refractometer. For high birefringence applications, a Δn of about 0.19 or more is preferred. Mixtures of dihalodiphenyldiacetylenes have Δn ranging from about 0.30 to 0.34. Dihalodiphenyldiacetylenes of the present invention can be admixed with compatible FLC materials and hosts to achieve high birefringence FLC materials. In particular, the 3,3'-difluorodiphenylacetylenes of the present invention are useful as FLC components to increase birefringence of an FLC material.

For certain applications of FLC materials, high tilt angle is a desirable property. High tilt is at least about 30°, more preferably at least about 35° and most preferably about 45°. The term tilt angle (Θ) refers to the saturation tilt angle of a smectic C or C* phase. Tilt angles can be determined by measurements in an SSFLC (or equivalent) cell. Specifically, a 2.5μM-spaced, polymer aligned SSFLC cell with indium-tin oxide conducting glass electrodes can be employed to measure tilt angles of the FLC materials of the present invention. Tilt angle is determined by rotating the shear or polymer aligned cell until extinction is obtained. The polarity of the cell is then reversed and the cell is rotated by a measured angle (2Θ) to obtain extinction again.

Tilt angle varies with temperature near the transition point between the C phase and a higher phase. Tilt angle can rapidly increase reaching saturation within a few degrees in temperature of the transition point (1st order behavior) or tilt angle can more slowly increase reaching saturation within 10°-20° C. below the transition temperature (2nd order behavior).

Tilt angles are typically measured at $T_C-T_X$, where $T_C$ and $T_X$ are the upper and lower transition temperatures for the C phase, respectively. The 3,3'-difluorophenyldiacetylenes of the present invention can be employed as FLC hosts which exhibit smectic C phases and on addition of FLC dopants exhibit high tilt angles in the smectic C* phase. High tilt FLC materials of the present invention comprise 50% or more by weight of a mixture of one or more 3',3'difluorodiphenylacetylene of formula C, more preferably comprise 75% or more by weight of a mixture of one or more of the 3,3'-difluorodiphenyldiacetylenes of formula C, and most preferably comprise 90% or more by weight of a mixture of one or more of the 3,3'difluorordiphenylacetylenes of formula C.

The 3,3'diflurordiphenyldiacetylenes of the present invention are useful as components of FLC materials and/or FLC host materials to create smectic C phase mixtures particularly those with a high tilt angle, and to increase birefringence in FLC materials.

EXAMPLES

Example 1: Synthesis of 4-alkoxyl, 3-fluorophenyl Acetylenes IV

The synthesis of the aromatic acetylene compounds of formula IV (Scheme I) are exemplified by the following synthesis of compound IV, where R is $C_{10}H_{21}$.

To a 50 ml round bottom flask was added 2.77 g (12.5 mmoles) 1-bromodecane and 2.39 g (12.5 mmoles) 2-fluoro-4-bromophenol (I) in 25 ml methyl ethyl ketone. 4.30 g anhydrous potassium carbonate was added and the heterogeneous mixture was refluxed for 48 hrs. The reaction mixture was partitioned between ethyl ether and water, washed with brine, dried, filtered through a 2 inch plug of silica, and solvent removed to afford 4.11 g (99%) of the 4-decyloxy-3-fluorophenyl bromide (II) where $R = C_{10}H_{21}$ as a pale yellow clear oil.

To a 250 ml round bottom flask equipped with magnetic stirrer and condenser was added 4.11 g of the 4-decyloxy-3-fluorophenyl bromide in 80 ml dry diisopropylamine. The palladium catalyst ($PdCl_3$, CuAc, $PPh_3$) (118 mg) followed by 1.453 g of trimethylsilyl acetylene was then added and the reaction refluxed for 48 hours. The reaction mixture was partitioned between hexane and water and the organic layer washed with water, brine, and dried with anhydrous magnesium sulfate. Removal of the solvent afforded 4.40 g of a brown oil. Flash chromatography (2% ethyl acetate/hexane) gave 4.11 g (96%) of TMS-protected acetylene (III), where $R = C_{10}H_{21}$, as a clear oil.

To a 250 ml round bottom flask equipped with a magnetic stirrer was added 4.11 g (11.8 mmoles) TMS-protected aromatic acetylene (III) and 2.0 g (35.4 mmoles) KOH in 120 ml of 1:1 MeOH/THF. The reaction mixture was stirred overnight at room temperature. After partitioning between diethyl ether and water, the organic phase was sequentially washed with water and brine and then dried with anhydrous magnesium sulfate affording 3.42 g of aromatic acetylene (IV where $R = C_{10}H_{21}$) 4-decyloxy-3-fluorophenyl acetylene as a rust colored oil.

Example 2: Synthesis of 4,4'-Dialkoxy-3,3'-difluoro diphenyldiacetylene (V)

The synthesis of the diphenyldiacetylenes of formula V (Scheme I) are exemplified by the following synthesis of compound V, where $R = C_{10}H_{21}$.

To a 50 ml round bottom flask equipped with a magnetic stirrer and reflux condenser was added 300 mg 4-decyloxy-3-fluorophenylacetylene and 43 mg cupric acetate in 40 ml 1:1 pyridine/MeOH. The reaction mixture was refluxed for 2 hrs, allowed to cool to room temperature and then added dropwise into a stirred 9 M aqueous sulfuric acid solution at ice bath temperature. The resulting cream-like suspension was extracted with ethyl ether and sequentially washed with water (3x) and brine and dried with anhydrous magnesium sulfate yielding 289 mg of a yellow-brown solid. Flash chromatography (1% ethyl acetate/hexane) and recrystallization of the residue from 95% ethanol afforded 248 mg diphenyldiacetylene (V), 4,4'-didecyloxy-3,3'-difluoro diphenyldiacetylene, as pale yellow needles.

Example 3: Mesomorphic Properties of 3,3'-Difluorodiphenyldiacetylenes (V)

The phase diagrams of compounds of formula V where $R = C_6H_{13}$, $C_8H_{17}$, $C_9H_{19}$, $C_{10}H_{21}$, $C_{11}H_{23}$, $C_{12}H_{25}$ and $C_{14}H_{29}$ are provided in Table I. In this Table and elsewhere in this application, except as noted, the following designations are employed: I=isotropic liquid, N=nematic, C= smectic C and X=crystal and transition temperatures are given in ° C. Phase transition temperatures and the nature of the phase transition were determined using Mettler Differential Thermal Analysis and optical polarized transmission microscopy.

Table II provides phase diagrams of nonhalogenated 4,4'-dialkoxydiphenyldiacetylenes (See Barrall et al. (1978) supra), for comparison to Table I. The didecyloxy substituted compound of Table II was prepared by methods analogous to those employed by Grant (1978) supra and phase diagrams were determined as noted above.

The compound of formula A where X=Y=Cl and $T_1=T_2 = C_{10}H_{21}O$, 4,4'-decyloxy-3,3'-dichlorodiphenylacetyene was synthesized by procedures analogous to those described in Scheme I and examples 1 and 2. The dichlorinated compound exhibited the following phase diagram:

having a narrow nematic phase and no observable smectic C phase.

The 2,2'-dihalogenated analogs of the compounds of formula C, 4,4'-didecyloxy-2,2'-difluoro diphenyldiacetylene and 4,4'-didecyloxy-2,2'-dichloro diphenyldiacetylene were synthesized by methods analogous to those exemplified in Scheme I and Examples 1 and 2. The 2,2'-difluoro compound exhibited the following phase diagram:

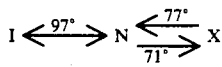

This compound exhibits a 20° C. enantiotropic nematic phase and no smectic phases were observed.

TABLE I

Mesomorphic Properties of 3,3'-difluorinated diphenyldiacetylenes (V)

| MDW # | Alkyl Tail | |
|---|---|---|
| 328 | $C_6H_{13}$ | I ⇄97° N ⇄56°/71° X |
| 329 | $C_8H_{17}$ | I ⇄92° N ⇄48°/61° C ⇄46° X |
| 332 | $C_9H_{19}$ | I ⇄88° N ⇄57°/63° C ⇄49° X |
| 308 | $C_{10}H_{21}$ | I ⇄88° N ⇄60° C ⇄40°/54° X |
| 333 | $C_{11}H_{23}$ | I ⇄86° N ⇄69° C ⇄41°/58° X |
| 324 | $C_{12}H_{25}$ | I ⇄86° N ⇄74° C ⇄40°/50° X |
| 325 | $C_{14}H_{29}$ | I ⇄84° N ⇄79° C ⇄50°/59° X |
| 392 | $C_{15}H_{31}$ | I ⇄84° N ⇄82° C ⇄56°/61° X |
| 393 | $C_{16}H_{33}$ | I ⇄85° N ⇄82° C ⇄58°/62° X |

TABLE II

| Alkyl Tail | Mesomorphic Properties of non-fluorinated diphenyldiacetylene |
|---|---|
| $C_6H_{13}$[1] | I ⇄149° N ⇄122° X |
| $C_8H_{17}$[1] | I ⇄135° N ⇄109° $Cr_1$ ⇄72° X |
| $C_{10}H_{21}$[2] | I ⇄127° N ⇄100° $Cr_1$ ⇄92° X |
| $C_{14}H_{29}$[1] | I ⇄116° N ⇄109° $Sm_2$ ⇄104° $Sm_1$ ⇄97° $Cr_1$ ⇄83° X |

[1]Barbara Grant, mol. Cryst. Liq. Cryst., 1978, 48, 175-182.
[2]The present work.

The 2,2'-dichloro compound exhibited the following phase diagram:

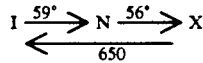

with a 3° C. monotropic nematic phase.

The compound of formula B where $T_3=T_4=C_{10}H_{19}$, 4,4'-didecyl-ω-eneoxy-3,3'-difluorodipheyldiacetylene was synthesized by methods analogous to those described in Scheme I and Examples 1 and 2. the dialkeneoxy compound exhibited the phase diagram:

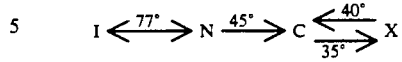

having a smectic C phase.

Example 4: Mesomorphic Properties of Mixtures of Diphenyldiacetylenes 1

A mixture made from equal parts of the four compounds of formula V having R=$C_8H_{17}$, $C_{10}H_{21}$, $C_{12}H_{25}$ and $C_{14}H_{29}$ straight-chain alkyl groups exhibited the phase diagram:

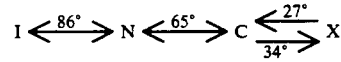

This formulation provides a eutectic mixture with a broad smectic C phase close to room temperature.

Example 5: Mesomorphic Properties of Mixtures of Difluorodiphenyldiacetylenes 2

A mixture made from equal parts of the five compounds of formula V having R=$C_9H_{19}$, $C_{10}H_{21}$, $C_{11}H_{23}$, $C_{12}H_{25}$ and $C_{14}H_{29}$ straight-chain alkyl groups exhibited the phase diagram:

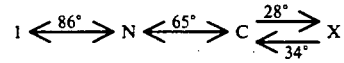

Example 6: Mesomorphic Properties of Mixtures of Difluorodiphenyldiacetylenes 3

A mixture made from equal parts of the three compounds of formula V having R=$C_{10}H_{21}$, $C_{11}H_{23}$ and $C_{14}H_{29}$ straight-chain alkyl groups exhibited the phase diagram:

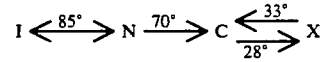

This formula provides a eutectic mixture with a smectic C phase close to room temperature.

Example 7: Mesomorphic Properties of Mixtures Comprising Difluorodiphenyldiacetylenes of Formula V To the mixture of Example 6, 25% by weight of 4,4'-didecyl-ω-eneoxy-3,3'-difluorodiphenyldiacetylene was added. The resultant mixture exhibited the phase diagram:

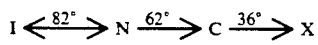

Addition of the dialkeneoxy compound to the mixture of alkoxyl components resulted in a narrowing of the smectic C phase: N→C transition was lowered by about 8° C. and the C→X transition was raised by about 3° C.

25% by weight of 4,4'-didecyloxy-3,3'-dichloro diphenyldiacetylene was added to the mixture of Example 6. The resultant mixture exhibited the phase diagram:

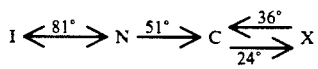

The N→C phase transition was lowered by about 20° C. and the C→X transition was raised by about 1° C.

Three mixtures were prepared by addition of 10% by weight of 4,4'-didecyloxy-2,2'-difluorodiphenylacetylene (MDW385), 4,4'-didecyloxy-2,2'-ditrifluoromethyldiphenyldiacetylene (MDW386) or 4,4'-didecyloxy-2,2'-dichloro diphenyldiacetylene (MDW387), respectively, to the mixture of Example 6 also designated MX5595. The resultant mixtures gave the following phase diagrams:

MDW285(10%)/MX5595

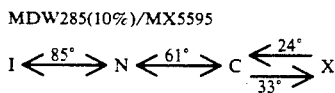

MDW386(10%)/MX5595

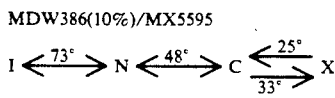

MDW387(10%)/MX5595

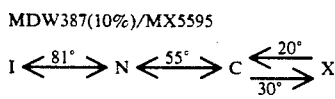

Example 8: High Tilt FLC Mixtures Comprising Difluorodiphenyldiacetylenes

To the mixture of Example 6, 2% (wt/wt, MDW116) a chiral, 2,3-difluoroalkoxylphenylpyrimidine FLC dopant prepared by methods of U.S. Serial No. 164,233, now allowed. The chiral resultant nonracemic FLC material displayed the phase diagram:

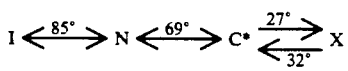

This FLC material was measured to have a tilt angle of 45° in the smectic C* phase.

Example 9: High Birefringence FLC Mixtures Comprising Difluorodiphenyldiacetylenes CS2004 is a commercially available high tilt FLC mixture (Chisso). The phase diagram of CS2004 is:

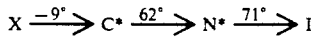

The mixture is believed to contain phenylpyrimidines and biphenylpyrimidines, exhibits a tilt angle of about 44° and was measured to have a birefringence (Δn) of 0.173. A mixture prepared by addition of 30% by weight of the difluorodiphenyldiacetylene mixture of Example 6 to CS2004 exhibited the phase diagram:

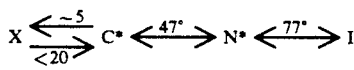

This mixture was measured to have a birefringence of 0.201. This mixture is, thus, a high birefringence, thermodynanucally stable broad C phase room temperature FLC material.

A high birefringence FLC mixture was prepared by combination of 62.5% of the mixture of Example 5, 25% CS2004 and 16.5% of a chiral nonracemic 3-ring tolane, designated MDW295:

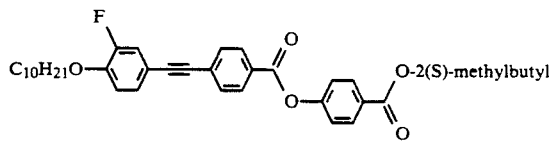

The mixture was found to have a birefringence of 0.245 and to exhibit the phase diagram:

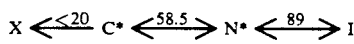

Those of ordinary skill in the art will readily appreciate that alternate techniques and procedures and functional equivalent materials other than those specifically described herein, can be employed to achieve the goals of the present invention. All such alternatives, varients and functional equivalents are considered to be encompassed by the spirit and scope of this invention.

We claim:

1. A compound of formula:

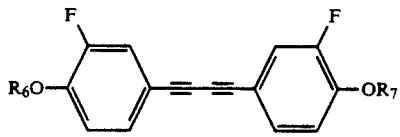

wherein $R_6$ and $R_7$, independently of one another, are straight-chain or branched alkyl groups having from three to twenty carbon atoms.

2. The compound of claim 1 wherein $R_6$ and $R_7$ are the same alkyl group.

3. The compound of claim 1 wherein $R_6$ and $R_7$, independently of one another, are straight-chain alkyl groups having from three to twenty carbon atoms.

4. The compound of claim 3 wherein $R_6$ equals $R_7$.

5. The compound of claim 1 wherein $R_6$ and $R_7$, independently of one another, are straight-chain alkyl groups having from eight to fourteen carbon atoms.

6. The compound of claim 5 wherein $R_6$ equals $R_7$.

7. The compound of claim wherein $R_6$ and $R_7$, independently of one another, are straight-chain alkyl groups having from nine to sixteen carbon atoms.

8. The compound of claim 7 wherein $R_6$ equals $R_7$.

9. The compound of claim 1 wherein $R_6$ and $R_7$, independently of one another, are straight-chain alkyl groups having from ten to twelve carbon atoms.

10. The compound of claim 9 wherein $R_6$ equals $R_7$.

11. A FLC material exhibiting a smectic C phase comprising about 75% or more by weight of a mixture of one or more of the compounds selected from the group consisting of 4,4'-didecyloxy-3,3'-difluorodiphenyldiacetylene, 4,4'-diundecyloxy-3,3'-difluorodiphenyldiacetylene and 4,4'-ditetradecyloxy-3,3'-difluorodiphenyldiacetylene.

12. A FLC host mixture which comprises one or more compounds having the formula:

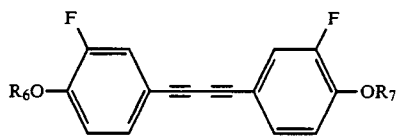

wherein $R_6$ and $R_7$, independently of one another, are straight-chain or branched alkyl groups having from three to twenty carbon atoms.

13. The FLC host of claim 12 wherein in said formula $R_6$ and $R_7$ are the same alkyl group.

14. The FLC host of claim 12 wherein in said formula $R_6$ and $R_7$, independently, of one another are straight chain alkyl groups having from three to twenty carbon atoms.

15. The FLC host of claim 14 wherein $R_6$ and $R_7$ are the same alkyl group.

16. The FLC host of claim 12 wherein in said formula $R_6$ and $R_7$, independently, of one another are straight chain alkyl groups having from eight to fourteen carbon atoms.

17. The FLC host of claim 16 wherein $R_6$ and $R_7$ are the same alkyl group.

18. A FLC material exhibiting a smectic C phase comprising about 75% or more by weight of a mixture of one or more compounds of formula:

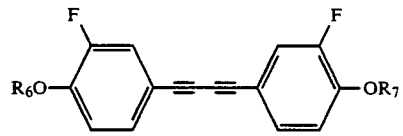

wherein $R_6$ and $R_7$, independently of one another, are straight-chain or branched alkyl groups having from three to twenty carbon atoms.

19. The FLC material of claim 18 wherein in said formula $R_6$ and $R_7$ are the same alkyl group.

20. The FLC material of claim 18 wherein in said formula $R_6$ and $R_7$, independently, of one another are straight chain alkyl groups having from three to twenty carbon atoms.

21. The FLC material of claim 20 wherein $R_6$ and $R_7$ are the same alkyl group.

22. The FLC material of claim 18 wherein in said formula $R_6$ and $R_7$, independently, of one another are straight chain alkyl groups having from eight to fourteen carbon atoms.

23. The FLC material of claim 22 wherein $R_6$ and $R_7$ are the same alkyl group.

24. A high birefringence FLC material exhibiting a smectic C phase comprising about 30% or more by weight of a mixture of one or more compounds of the formula:

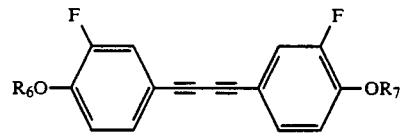

wherein $R_6$ and $R_7$, independently of one another, are straight-chain or branched alkyl groups having from three to twenty carbon atoms.

25. The FLC material of claim 24 wherein in said formula $R_6$ and $R_7$ are the same alkyl group.

26. The FLC material of claim 24 wherein in said formula $R_6$ and $R_7$, independently, of one another are straight chain alkyl groups having from three to twenty carbon atoms.

27. The FLC material of claim 26 wherein $R_6$ and $R_7$ are the same alkyl group.

28. The FLC material of claim 24 wherein in said formula $R_6$ and $R_7$, independently, of one another are straight chain alkyl groups having from eight to fourteen carbon atoms.

29. The FLC material of claim 28 wherein $R_6$ and $R_7$ are the same alkyl group.

* * * * *

UNITED STATES PATENT AND TRADEMARK OFFICE
CERTIFICATE OF CORRECTION

PATENT NO. : 5,178,791

DATED : Jan. 12, 1993

INVENTOR(S) : Michael D. Wand; Sean D. Monahan

It is certified that error appears in the above-identified patent and that said Letters Patent is hereby corrected as shown below:

At column 1, line 28, please rewrite "filed" as --field--. At column 6, bridging lines 13-15, please rewrite "mesophoric" as --mesomorphic--. At column 8, line 27, please rewrite "mescribility" as --miscibility--. At column 8, line 29, please rewrite "mesophoric" as --mesomorphic--. At column 9, line 18, please rewrite "3',3'difluorodiphenyl-acetylenes" as --3,3'difluorodiphenylacetylenes--. At column 9, bridging lines 23-24, please rewrite "3,3'-difluorordiphenylacetylenes" as --3,3'-difluorodiphenyldiacetylenes--. At column 9, line 25, please rewrite "3,3'-diflurordiphenyldiacetylenes" as --3,3'-difluorodiphenyl-diacetylenes--. At column 9, line 32, please rewrite "4-alkoxy-3-fluorophenvl" as --4-alkoxy-3-fluorophenyl--. At column 9, line 50, please rewrite "($PdCl_3$," as --($PdCl_2$,--. At column 11, line 67, please rewrite "4,4'-didecyl-ω-eneoxy-3,3'-difluorodipheyldiacetylene" as --4,4'-didecyl-ω-eneoxy-3,3'-difluorodiphenyldiacetylene--. At column 14, line 19, please rewrite "thermodynanucally" as --thermodynamically--. At column 15, line 1, please insert --1-- between "claim" and "wherein".

Signed and Sealed this

Sixth Day of December, 1994

Attest:

Attesting Officer

BRUCE LEHMAN

Commissioner of Patents and Trademarks